US012583813B2

(12) United States Patent
Gorges et al.

(10) Patent No.: US 12,583,813 B2
(45) Date of Patent: Mar. 24, 2026

(54) POLYMERIZATION INHIBITORS

(71) Applicant: BASF SE, Ludwigshafen am Rhein (DE)

(72) Inventors: Jan Niclas Gorges, Ludwigshafen am Rhein (DE); Rebecca Sure, Ludwigshafen am Rhein (DE); Friederike Fleischhaker, Ludwigshafen am Rhein (DE); Friedrich-Georg Martin, Ludwigshafen am Rhein (DE); Christian Rein, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 635 days.

(21) Appl. No.: 18/000,519

(22) PCT Filed: May 25, 2021

(86) PCT No.: PCT/EP2021/063807
§ 371 (c)(1),
(2) Date: Dec. 2, 2022

(87) PCT Pub. No.: WO2021/244894
PCT Pub. Date: Dec. 9, 2021

(65) Prior Publication Data

US 2023/0242472 A1 Aug. 3, 2023

(30) Foreign Application Priority Data

Jun. 5, 2020 (EP) .................................... 20178453

(51) Int. Cl.
*C07C 67/62* (2006.01)
*C07C 43/23* (2006.01)
*C07C 51/50* (2006.01)

(52) U.S. Cl.
CPC .............. *C07C 67/62* (2013.01); *C07C 43/23* (2013.01); *C07C 51/50* (2013.01)

(58) Field of Classification Search
CPC .......... C07C 67/62; C07C 51/50; C07C 43/23
See application file for complete search history.

(56) References Cited

U.S. PATENT DOCUMENTS

| | | | |
|---|---|---|---|
| 3,356,663 | A | 12/1967 | Richard et al. |
| 2021/0139515 | A1 | 5/2021 | Nyuugaku |

FOREIGN PATENT DOCUMENTS

| | | | | |
|---|---|---|---|---|
| EP | 3819301 A1 | | 5/2021 | |
| GB | 1011315 | * | 11/1965 | ............ C07C 67/62 |
| GB | 1011315 A | | 11/1965 | |

OTHER PUBLICATIONS

Burton G W et al. Autoxidation of biological molecules. 4. Maximizing the antioxidant activity of phenols, Journal of the American Chemical Society, American Chemical Society, vol. 107, No. 24, 1985, pp. 7053-7065.
International Preliminary Report on Patentability received for PCT Patent Application No. PCT/EP2021/063807, mailed on Dec. 15, 2022, 15 pages (9 pages of English Translation and 6 pages of Original Document).
International Search Report and Written Opinion received for PCT Patent Application No. PCT/EP2021/063807, Issued on Aug. 26, 2021, 8 pages.
Anonymous, et al., "Chapter 7: Bulk Storage Facilities and Accessories", Acrylic Acid A Summary of Safety and Handling, Fourth Edition, Compiled by Basic Acrylic Monomer Manufacturers, Inc., 2013, pp. 12-22.
Anonymous, et al., "Chapter 9: Safe Transport of Acrylic Acid", Acrylic Acid A Summary of Safety and Handling, Fourth Edition, Compiled by Basic Acrylic Monomer Manufacturers, Inc., 2013, pp. 24-34.

* cited by examiner

*Primary Examiner* — Yate' K Cutliff
(74) *Attorney, Agent, or Firm* — Faeger Drinker Biddle & Reath LLP

(57) ABSTRACT

The present invention relates to a mixture comprising at least one substituted hydroquinone monoether and at least one polymerizable compound.

16 Claims, No Drawings

POLYMERIZATION INHIBITORS

CROSS-REFERENCE TO RELATED APPLICATIONS

This application is a National stage application (under 35 U.S.C. § 371) of PCT/EP2021/063807, filed May 25, 2021, which claims benefit of European Application No. 20178453.5, filed Jun. 5, 2020, both of which are incorporated herein by reference in their entirety.

The present invention relates to a mixture comprising at least one substituted hydroquinone monoether and at least one polymerizable compound.

Chemical compounds comprising one or more ethylenically unsaturated groups have a pronounced tendency to free-radical polymerization. Such compounds are accordingly referred to as polymerizable compounds below. The tendency of these compounds to free-radical polymerization means that they are used as monomers for the production of polymers. However, the pronounced tendency to free-radical polymerization of these compounds is also a disadvantage in that undesired spontaneous free-radical polymerization can occur during storage and transport and also during chemical and physical processing such as distillation or rectification, particularly under the action of energy such as heat and/or light. Such uncontrolled polymerizations can result in the gradual formation of polymer deposits, for example on heated surfaces, that necessitates removal of the polymer deposits and thus often results in shortened operating times. The uncontrolled polymerizations may even proceed explosively.

During storage and transport and also during chemical and/or physical processing of ethylenically unsaturated compounds that have a tendency to free-radical polymerization or mixtures that comprise such compounds, it is therefore customary to add compounds that prevent or at least retard undesired spontaneous free-radical polymerization. Such substances are often referred to as polymerization inhibitors.

Polymerization inhibitors may be employed as individual chemical compounds or as mixtures of compounds. Depending on the field of application of the polymerization inhibitor, said inhibitor may have particular demands made of it. For a polymerization inhibitor to be suitable as a transport and/or storage stabilizer of ethylenically unsaturated compounds it is important that the efficiency of the polymerization inhibitor, i.e. the extent of polymerization inhibition, is controllable. Under the conditions of storage and/or transport of the ethylenically unsaturated compounds, the polymerization inhibitor should adequately prevent or retard undesired spontaneous free-radical polymerization, whereas the desired free-radical polymerization of the ethylenically unsaturated compounds should be possible under appropriate polymerization conditions without the need to first have to separate the polymerization inhibitor used during storage and/or transport. If the stabilizer used during storage and/or transport is not separated for the desired polymerization it is important that it does not adversely affect the desired polymerization, for example unintentionally act as chain-transfer agent.

In terms of global production volume, acrylic acid is without doubt one of the most important ethylenically unsaturated compounds. Acrylic acid is as standard stabilized against undesired spontaneous free-radical polymerization with 0.018% to 0.022% by weight of hydroquinone monomethyl ether (MEHQ) based on the amount of acrylic acid during storage and/or transport. For adequate stabilization of acrylic acid against undesired spontaneous free-radical polymerization using MEHQ, it is necessary that oxygen is dissolved in the acrylic acid in sufficient amounts. Sufficient amounts of oxygen are generally dissolved in the acrylic acid when acrylic acid is stored and/or transported in an atmosphere comprising 5 to 21 vol % of oxygen. In the desired polymerization of acrylic acid the content of dissolved oxygen in the acrylic acid is reduced, thus reducing the efficiency of MEHQ as a polymerization inhibitor enough for acrylic acid to undergo polymerization in the presence of MEHQ.

In addition to use as a polymerization inhibitor for storage and/or transport of acrylic acid, MEHQ is also used as a polymerization inhibitor for storage and/or transport of methacrylic acid, acrylic esters and/or methacrylic esters or of mixtures comprising one or more of said compounds.

As a consequence of widespread use MEHQ is one of the most important storage and/or transport stabilizers for polymerizable compounds, especially for acrylic acid, methacrylic acid, acrylic esters and methacrylic esters.

Polymerizable compounds are stored in suitable permanently installed containers, such as storage tanks or storage vessels (see for example Acrylic Acid, A Summary of Safety and Handling, 4th edition 2013, 7 Bulk Storage Facilities and Accessories). Storage of the polymerizable compounds in the respective containers is preferably for at least one minute, particularly preferably at least 10 minutes, very particularly preferably at least 60 minutes. Although the duration of storage under appropriate conditions is theoretically unlimited, the duration of storage is generally reduced to a minimum for economic reasons. Storage of the polymerizable compounds in the respective containers is preferably for not more than 180 days, particularly preferably for not more than 90 days, very particularly preferably for not more than 30 days. Particularly preferred ranges arise from the free combination of the abovementioned lower and upper ranges.

Polymerizable compounds are normally transported in suitable transportable containers such as tanks or vessels by ship, rail and/or truck (see for example Acrylic Acid, A Summary of Safety and Handling, 4th edition 2013, 9 Safe Transport of Acrylic Acid). The transportable containers may of course also be permanently installed on the corresponding means of transportation, for example tanker ships or rail tank cars. It is of course also possible for containers to be stored for a certain time in a particular place before the transport thereof somewhere else. Transport of polymerizable compounds may also be effected in pipelines or hoses, for example to a storage tank after purification of the polymerizable compounds, during loading from the storage tank into a transportable container, and/or during loading from one transportable container into another. It is preferable when transport of the polymerizable compounds in the respective containers is for at least 10 seconds, preferably at least one minute, particularly preferably at least 10 minutes, very particularly preferably at least 60 minutes. Although the duration under appropriate conditions is theoretically unlimited, the duration is generally reduced to a minimum for economic and safety reasons. Transport of the polymerizable compounds in the respective containers is preferably for not more than 180 days, particularly preferably for not more than 90 days, very particularly preferably for not more than 30 days. Particularly preferred ranges arise from the free combination of the abovementioned lower and upper ranges.

It is an object of the present invention to provide mixtures comprising at least one polymerizable compound, in particular acrylic acid, methacrylic acid, acrylic esters and/or methacrylic esters, and at least one polymerization inhibitor. The polymerization inhibitors shall ensure sufficient stabilization of the polymerizable compounds against undesired free-radical polymerization. However, for the desired free-radical polymerization there shall be no need to remove the polymerization inhibitors from the mixture prior to the polymerization. The polymerization inhibitors therefore shall not act as chain-transfer agents and/or polymerization inhibitors in the desired free-radical polymerization.

The object is achieved by mixtures comprising at least one compound of general formula (I), (I)

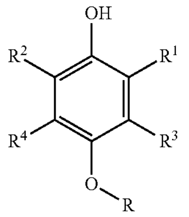

wherein

- R is $C_1$- to $C_4$-alkyl, preferably $C_1$- to $C_3$-alkyl, particularly preferably $C_1$- or $C_2$-alkyl, very particularly preferably $C_1$-alkyl,
- $R^1$ is $C_1$- or $C_2$-alkyl, very particularly preferably $C_1$-alkyl and
- $R^2$ to $R^4$ are independently of one another H, $C_1$- or $C_2$-alkyl, very particularly preferably independently of one another H or $C_1$-alkyl, and at least one polymerizable compound.

Particular preference is given to mixtures comprising one or more compounds of general formula (I), wherein

- R is $C_1$- to $C_4$-alkyl, preferably $C_1$- to $C_3$-alkyl, particularly preferably $C_1$- or $C_2$-alkyl, very particularly preferably $C_1$-alkyl,
- $R^1$ and $R^2$ are independently of one another $C_1$- or $C_2$-alkyl, very particularly preferably $C_1$-alkyl, and
- $R^3$ and $R^4$ are independently of one another H, $C_1$- or $C_2$-alkyl, very particularly preferably independently of one another H or $C_1$-alkyl, and at least one polymerizable compound.

Very particular preference is given to mixtures comprising one or more compounds of general formula (I), wherein

- R is $C_1$- to $C_4$-alkyl, preferably $C_1$- to $C_3$-alkyl, particularly preferably $C_1$- or $C_2$-alkyl, very particularly preferably $C_1$-alkyl,
- $R^1$, $R^2$ and $R^3$ are independently of one another $C_1$- or $C_2$-alkyl, very particularly preferably $C_1$-alkyl, and
- $R^4$ is H, $C_1$- or $C_2$-alkyl, very particularly preferably H or $C_1$-alkyl, and at least one polymerizable compound.

Suitable compounds of general formula (I) are for example 2-methyl-4-methoxy-phenol, 2,3-dimethyl-4-methoxy-phenol, 2,5-dimethyl-4-methoxy-phenol, 2,6-dimethyl-4-methoxy-phenol, 2,3,5-trimethyl-4-methoxy-phenol, 2,3,6-trimethyl-4-methoxy-phenol, 2,3,5,6-tetramethyl-4-methoxy-phenol, 2-ethyl-4-methoxy-phenol, 2-ethyl-3-methyl-4-methoxy-phenol, 2-methyl-3-ethyl-4-methoxy-phenol, 2-ethyl-5-methyl-4-methoxy-phenol, 2-methyl-5-ethyl-4-methoxy-phenol, 2-ethyl-6-methyl-4-methoxy-phenol, 2-methyl-6-ethyl-4-methoxy-phenol, 2-ethyl-3,5-dimethyl-4-methoxy-phenol, 2,3-dimethyl-5-ethyl-4-methoxy-phenol, 2,5-dimethyl-3-ethyl-4-methoxy-phenol, 2-ethyl-3,6-dimethyl-4-methoxy-phenol, 2,3-dimethyl-6-ethyl-4-methoxy-phenol, 2,6-dimethyl-3-ethyl-4-methoxy-phenol, 2-ethyl-3,5,6-trimethyl-4-methoxy-phenol, 2,5,6-trimethyl-3-ethyl-4-methoxy-phenol, 2,3-diethyl-4-methoxy-phenol, 2,5-diethyl-4-methoxy-phenol, 2,6-diethyl-4-methoxy-phenol, 2-methyl-3,5-diethyl-4-methoxy-phenol, 2,3-diethyl-5-methyl-4-methoxy-phenol, 2,5-diethyl-3-methyl-4-methoxy-phenol, 2-methyl-3,6-diethyl-4-methoxy-phenol, 2,3-diethyl-6-methyl-4-methoxy-phenol, 2,6-diethyl-3-methyl-4-methoxy-phenol, 2,3-diethyl-5,6-dimethyl-4-methoxy-phenol, 2,5-diethyl-3,6-dimethyl-4-methoxy-phenol, 2,6-diethyl-3,5-dimethyl-4-methoxy-phenol, 2,3,5-triethyl-6-methyl-4-methoxy-phenol, 2,3,6-triethyl-5-methyl-4-methoxy-phenol, 2,3,5,6-tetraethyl-4-methoxy-phenol, 2-methyl-4-ethoxy-phenol, 2,3-dimethyl-4-ethoxy-phenol, 2,5-dimethyl-4-ethoxy-phenol, 2,6-dimethyl-4-ethoxy-phenol, 2,3,5-trimethyl-4-ethoxy-phenol, 2,3,6-trimethyl-4-ethoxy-phenol, 2,3,5,6-tetramethyl-4-ethoxy-phenol, 2-ethyl-4-ethoxy-phenol, 2-ethyl-3-methyl-4-ethoxy-phenol, 2-methyl-3-ethyl-4-ethoxy-phenol, 2-ethyl-5-methyl-4-ethoxy-phenol, 2-methyl-5-ethyl-4-ethoxy-phenol, 2-ethyl-6-methyl-4-ethoxy-phenol, 2-methyl-6-ethyl-4-ethoxy-phenol, 2-ethyl-3,5-dimethyl-4-ethoxy-phenol, 2,3-dimethyl-5-ethyl-4-ethoxy-phenol, 2,5-dimethyl-3-ethyl-4-ethoxy-phenol, 2-ethyl-3,6-dimethyl-4-ethoxy-phenol, 2,3-dimethyl-6-ethyl-4-ethoxy-phenol, 2,6-dimethyl-3-ethyl-4-ethoxy-phenol, 2-ethyl-3,5,6-trimethyl-4-ethoxy-phenol, 2,5,6-trimethyl-3-ethyl-4-ethoxy-phenol, 2,3-diethyl-4-ethoxy-phenol, 2,5-diethyl-4-ethoxy-phenol, 2,6-diethyl-4-ethoxy-phenol, 2-methyl-3,5-diethyl-4-ethoxy-phenol, 2,3-diethyl-5-methyl-4-ethoxy-phenol, 2,5-diethyl-3-methyl-4-ethoxy-phenol, 2-methyl-3,6-diethyl-4-ethoxy-phenol, 2,3-diethyl-6-methyl-4-ethoxy-phenol, 2,6-diethyl-3-methyl-4-ethoxy-phenol, 2,3-diethyl-5,6-dimethyl-4-ethoxy-phenol, 2,5-diethyl-3,6-dimethyl-4-ethoxy-phenol, 2,6-diethyl-3,5-dimethyl-4-ethoxy-phenol, 2,3,5-triethyl-6-methyl-4-ethoxy-phenol, 2,3,6-triethyl-5-methyl-4-ethoxy-phenol, 2,3,5,6-tetraethyl-4-ethoxy-phenol, 2-methyl-4-propoxy-phenol, 2,3-dimethyl-4-propoxy-phenol, 2,5-dimethyl-4-propoxy-phenol, 2,6-dimethyl-4-propoxy-phenol, 2,3,5-trimethyl-4-propoxy-phenol, 2,3,6-trimethyl-4-propoxy-phenol, 2,3,5,6-tetramethyl-4-propoxy-phenol, 2-ethyl-4-propoxy-phenol, 2-ethyl-3-methyl-4-propoxy-phenol, 2-methyl-3-ethyl-4-propoxy-phenol, 2-ethyl-5-methyl-4-propoxy-phenol, 2-methyl-5-ethyl-4-30 propoxy-phenol, 2-ethyl-6-methyl-4-propoxy-phenol, 2-methyl-6-ethyl-4-propoxy-phenol, 2-ethyl-3,5-dimethyl-4-propoxy-phenol, 2,3-dimethyl-5-ethyl-4-propoxy-phenol, 2,5-dimethyl-3-ethyl-4-propoxy-phenol, 2-ethyl-3,6-dimethyl-4-propoxy-phenol, 2,3-dimethyl-6-ethyl-4-propoxy-phenol, 2,6-dimethyl-3-ethyl-4-propoxy-phenol, 2-ethyl-3,5,6-trimethyl-4-propoxy-phenol, 2,5,6-trimethyl-3-ethyl-4-propoxy-phenol, 2,3-diethyl-4-propoxy-phenol, 2,5-diethyl-4-propoxy-phenol, 2,6-diethyl-4-propoxy-phenol, 2-methyl-3,5-diethyl-4-propoxy-phenol, 2,3-diethyl-5-methyl-4-propoxy-phenol, 2,5-diethyl-3-methyl-4-propoxy-phenol, 2-methyl-3,6-diethyl-4-propoxy-phenol, 2,3-diethyl-6-methyl-4-propoxy-phenol, 2,6-diethyl-3-methyl-4-propoxy-phenol, 2,3-diethyl-5,6-dimethyl-4-propoxy-phenol, 2,5-diethyl-3,6-dimethyl-4-propoxy-phenol, 2,6-diethyl-3,5-dimethyl-4-propoxy-phenol, 2,3,5-triethyl-6-methyl-4-propoxy-phenol, 2,3,6-triethyl-5-methyl-4-propoxy-phenol, 2,3,5,6-tetraethyl-4-propoxy-phenol, 2-methyl-4-isopropoxy-phenol, 2,3-dimethyl-4-isopropoxy-phenol, 2,5-dimethyl-4-isopropoxy-phenol, 2,6-dimethyl-4-isopropoxy-phenol, 2,3,5- trimethyl-4-isopropoxy-phenol, 2,3,6-trimethyl-4-isopropoxy-phenol, 2,3,5,6-tetramethyl-4-isopropoxy-phenol, 2-ethyl-4-isopropoxy-phenol, 2-ethyl-3-methyl-4-isopropoxy-phenol, 2-methyl-3-ethyl-4-isopropoxy-phenol, 2-ethyl-5-methyl-4-isopropoxy-phenol, 2-methyl-5-ethyl-4-isopropoxy-phenol, 2-ethyl-6-methyl-4-isopropoxy-phenol, 2-methyl-6-ethyl-4-isopropoxy-phenol, 2-ethyl-3,5-dimethyl-4-isopropoxy-phenol, 2,3-dimethyl-5-ethyl-4-isopropoxy-phenol, 2,5-dimethyl-3-ethyl-4-isopropoxy-phenol, 2-ethyl-3,6-dimethyl-4-isopropoxy-phenol, 2,3-dimethyl-6-ethyl-4-isopropoxy-phenol, 2,6-dimethyl-3-ethyl-4-isopropoxy-phenol, 2-ethyl-3,5,6-trimethyl-4-isopropoxy-phenol, 2,5,6-trimethyl-3-ethyl-4-isopropoxy-phenol, 2,3-diethyl-4-isopropoxy-phenol, 2,5-diethyl-4-isopropoxy-phenol, 2,6-diethyl-4-isopropoxy-phenol, 2-methyl-3,5-diethyl-4-isopropoxy-phenol, 2,3-diethyl-5-methyl-4-isopropoxy-phenol, 2,5-diethyl-3-methyl-4-isopropoxy-phenol, 2-methyl-3,6-diethyl-4-isopropoxy-phenol, 2,3-diethyl-6-methyl-4-isopropoxy-phenol, 2,6-diethyl-3-methyl-4-isopropoxy-phenol, 2,3-diethyl-5,6-dimethyl-4-isopropoxy-phenol, 2,5-diethyl-3,6-dimethyl-4-isopropoxy-phenol, 2,6-diethyl-3,5-dimethyl-4-isopropoxy-phenol, 2,3,5-triethyl-6-methyl-4-isopropoxy-phenol, 2,3,6-triethyl-5-methyl-4-isopropoxy-phenol, 2,3,5,6-tetraethyl-4-isopropoxy-phenol, 2-methyl-4-butoxy-phenol, 2,3-dimethyl-4-butoxy-phenol, 2,5-dimethyl-4-butoxy-phenol, 2,6-dimethyl-4-butoxy-phenol, 2,3,5-trimethyl-4-butoxy-phenol, 2,3,6-trimethyl-4-butoxy-phenol, 2,3,5,6-tetramethyl-4-butoxy-phenol, 2-ethyl-4-butoxy-phenol, 2-ethyl-3-methyl-4-butoxy-phenol, 2-methyl-3-ethyl-4-butoxy-phenol, 2-ethyl-5-methyl-4-butoxy-phenol, 2-methyl-5-ethyl-4-butoxy-phenol, 2-ethyl-6-methyl-4-butoxy-phenol, 2-methyl-6-ethyl-4-butoxy-phenol, 2-ethyl-3,5-dimethyl-4-butoxy-phenol, 2,3-dimethyl-5-ethyl-4-butoxy-phenol, 2,5-dimethyl-3-ethyl-4-butoxy-phenol, 2-ethyl-3,6-dimethyl-4-butoxy-phenol, 2,3-dimethyl-6-ethyl-4-butoxy-phenol, 2,6-dimethyl-3-ethyl-4-butoxy-phenol, 2-ethyl-3,5,6-trimethyl-4-butoxy-phenol, 2,5,6-trimethyl-3-ethyl-4-butoxy-phenol, 2,3-diethyl-4-butoxy-phenol, 2,5-diethyl-4-butoxy-phenol, 2,6-diethyl-4-butoxy-phenol, 2-methyl-3,5-diethyl-4-butoxy-phenol, 2,3-diethyl-5-methyl-4-butoxy-phenol, 2,5-diethyl-3-methyl-4-butoxy-phenol, 2-methyl-3,6-diethyl-4-butoxy-phenol, 2,3-diethyl-6-methyl-4-butoxy-phenol, 2,6-diethyl-3-methyl-4-butoxy-phenol, 2,3-diethyl-5,6-dimethyl-4-butoxy-phenol, 2,5-diethyl-3,6-dimethyl-4-butoxy-phenol, 2,6-diethyl-3,5-dimethyl-4-butoxy-phenol, 2,3,5-triethyl-6-methyl-4-butoxy-phenol, 2,3,6-triethyl-5-methyl-4-butoxy-phenol, 2,3,5,6-tetraethyl-4-butoxy-phenol, 2-methyl-4-isobutoxy-phenol, 2,3-dimethyl-4-isobutoxy-phenol, 2,5-dimethyl-4-isobutoxy-phenol, 2,6-dimethyl-4-isobutoxy-phenol, 2,3,5-trimethyl-4-isobutoxy-phenol, 2,3,6-trimethyl-4-isobutoxy-phenol, 2,3,5,6-tetramethyl-4-isobutoxy-phenol, 2-ethyl-4-isobutoxy-phenol, 2-ethyl-3-methyl-4-isobutoxy-phenol, 2-methyl-3-ethyl-4-isobutoxy-phenol, 2-ethyl-5-methyl-4-isobutoxy-phenol, 2-methyl-5-ethyl-4-isobutoxy-phenol, 2-ethyl-6-methyl-4-isobutoxy-phenol, 2-methyl-6-ethyl-4-isobutoxy-phenol, 2-ethyl-3,5-dimethyl-4-isobutoxy-phenol, 2,3-dimethyl-5-ethyl-4-isobutoxy-phenol, 2,5-dimethyl-3-ethyl-4-isobutoxy-phenol, 2-ethyl-3,6-dimethyl-4-isobutoxy-phenol, 2,3-dimethyl-6-ethyl-4-isobutoxy-phenol, 2,6-dimethyl-3-ethyl-4-isobutoxy-phenol, 2-ethyl-3,5,6-trimethyl-4-isobutoxy-phenol, 2,5,6-trimethyl-3-ethyl-4-isobutoxy-phenol, 2,3-diethyl-4-isobutoxy-phenol, 2,5-diethyl-4-isobutoxy-phenol, 2,6-diethyl-4-isobutoxy-phenol, 2-methyl-3,5-diethyl-4-isobutoxy-phenol, 2,3-diethyl-5-methyl-4-isobutoxy-phenol, 2,5-diethyl-3-methyl-4-isobutoxy-phenol, 2-methyl-3,6-diethyl-4-isobutoxy-phenol, 2,3-diethyl-6-methyl-4-isobutoxy-phenol, 2,6-diethyl-3-methyl-4-isobutoxy-phenol, 2,3-diethyl-5,6-dimethyl-4-isobutoxy-phenol, 2,5-diethyl-3,6-dimethyl-4-isobutoxy-phenol, 2,6-diethyl-3,5-dimethyl-4-isobutoxy-phenol, 2,3,5-triethyl-6-methyl-4-isobutoxy-phenol, 2,3,6-triethyl-5-methyl-4-isobutoxy-phenol, 2,3,5,6-tetraethyl-4-isobutoxy-phenol, 2-methyl-4-tert.-butoxy-phenol, 2,3-dimethyl-4-tert.-butoxy-phenol, 2,5-dimethyl-4-tert.-butoxy-phenol, 2,6-dimethyl-4-tert.-butoxy-phenol, 2,3,5-trimethyl-4-tert.-butoxy-phenol, 2,3,6-trimethyl-4-tert.-butoxy-phenol, 2,3,5,6-tetramethyl-4-tert.-butoxy-phenol, 2-ethyl-4-tert.-butoxy-phenol, 2-ethyl-3-methyl-4-tert.-butoxy-phenol, 2-methyl-3-ethyl-4-tert.-butoxy-phenol, 2-ethyl-5-methyl-4-tert.-butoxy-phenol, 2-methyl-5-ethyl-4-tert.-butoxy-phenol, 2-ethyl-6-methyl-4-tert.-butoxy-phenol, 2-methyl-6-ethyl-4-tert.-butoxy-phenol, 2-ethyl-3,5-dimethyl-4-tert.-butoxy-phenol, 2,3-dimethyl-5-ethyl-4-tert.-butoxy-phenol, 2,5-dimethyl-3-ethyl-4-tert.-butoxy-phenol, 2-ethyl-3,6-dimethyl-4-tert.-butoxy-phenol, 2,3-dimethyl-6-ethyl-4-tert.-butoxy-phenol, 2,6-dimethyl-3-ethyl-4-tert.-butoxy-phenol, 2-ethyl-3,5,6-trimethyl-4-tert.-butoxy-phenol, 2,5,6-trimethyl-3-ethyl-4-tert.-butoxy-phenol, 2,3-diethyl-4-tert.-butoxy-phenol, 2,5-diethyl-4-tert.-butoxy-phenol, 2,6-diethyl-4-tert.-butoxy-phenol, 2-methyl-3,5-diethyl-4-tert.-butoxy-phenol, 2,3-diethyl-5-methyl-4-tert.-butoxy-phenol, 2,5-diethyl-3-methyl-4-tert.-butoxy-phenol, 2-methyl-3,6-diethyl-4-tert.-butoxy-phenol, 2,3-diethyl-6-methyl-4-tert.-butoxy-phenol, 2,6-diethyl-3-methyl-4-tert.-butoxy-phenol, 2,3-diethyl-5,6-dimethyl-4-tert.-butoxy-phenol, 2,5-diethyl-3,6-dimethyl-4-tert.-butoxy-phenol, 2,6-diethyl-3,5-dimethyl-4-tert.-butoxy-phenol, 2,3,5-triethyl-6-methyl-4-tert.-butoxy-phenol, 2,3,6-triethyl-5-methyl-4-tert.-butoxy-phenol and 2,3,5,6-tetraethyl-4-tert.-butoxy-phenol.

In the mixture the total amount of the compounds of general formula (I) is preferably from 0.0001% to 0.1000% by weight, preferably from 0.0002% to 0.0750% by weight, particularly preferably from 0.0005% to 0.0500% by weight, very particularly preferably from 0.0010% to 0.0250% by weight, in each case based on the total amount of polymerizable compounds.

In the mixture the total amount of polymerizable compounds is preferably at least 5% by weight, preferably at least 50% by weight, particularly preferably at least 80% by weight, very particularly preferably at least 99% by weight, in each case based on the total weight of the mixture.

Polymerizable compounds are preferably mono-, di- or triethylenically unsaturated $C_3$- to $C_8$-carboxylic acids, mono-, di- or triethylenically unsaturated $C_3$- to $C_8$-aldehydes, mono-, di- or triethylenically unsaturated $C_3$- to $C_8$-carboxylic esters having 1 to 20 carbon atoms in the ester groups, mono-, di- or triethylenically unsaturated $C_3$- to $C_8$-carboxamides, mono-, di- or triethylenically unsaturated $C_3$- to $C_8$-nitriles, mono-, di- or triethylenically unsaturated $C_3$- to $C_8$-carboxylic anhydrides, vinyl esters of saturated $C_2$- to $C_{20}$-carboxylic acids, vinyl ethers of saturated $C_1$- to $C_{10}$-alcohols, vinylaromatics, vinyl heteroaromatics, vinyl lactams having 3 to 10 carbon atoms in the ring, open-chain N-vinylamide compounds and N-vinylamine compounds, vinyl halides, aliphatic, optionally halogenated, hydrocarbons having 2 to 8 carbon atoms and 1 or 2 ethylenic double bonds, vinylidenes or any desired mixtures of two or more of the abovementioned compounds.

Particular preference is given to mono-, di- or triethylenically unsaturated $C_3$- to $C_8$-carboxylic acids, for example acrylic acid, methacrylic acid, dimethacrylic acid, ethacrylic acid, citraconic acid, methylenemalonic acid, crotonic acid, fumaric acid, mesaconic acid, itaconic acid and maleic acid, mono-, di- or triethylenically unsaturated $C_3$- to $C_8$-carboxylic acids having 1 to 20 carbon atoms in the ester groups, for example acrylic esters with $C_1$- to $C_{20}$-alkyl, methacrylate esters with $C_1$- to $C_{20}$-alkyl, dimethacrylate esters with $C_1$- to $C_{20}$-alkyl, ethacrylate esters with $C_1$- to $C_{20}$-alkyl, citraconate esters with $C_1$- to $C_{20}$-alkyl, methylenemalonate esters with $C_1$- to $C_{20}$-alkyl, crotonate esters with $C_1$- to $C_{20}$-alkyl, fumarate esters with $C_1$- to $C_{20}$-alkyl, mesaconate esters with $C_1$- to $C_{20}$-alkyl, itaconate esters with $C_1$- to $C_{20}$-alkyl and maleate esters with $C_1$- to $C_{20}$-alkyl, mono-, di- or triethylenically unsaturated $C_3$- to $C_8$-carboxamides, for example acrylamide, methacrylamide, dimethacrylamide, ethacrylamide, citraconamide, methylenemalonamide, crotonamide, fumaramide, mesaconamide, itaconamide and maleamide, mono-, di- or triethylenically unsaturated $C_3$- to $C_8$-nitriles, for example acrylonitrile and methacrylonitrile, and mono-, di- or triethylenically unsaturated $C_3$- to $C_8$-carboxylic anhydrides, for example acrylic anhydride, methacrylic anhydride, itaconic anhydride and maleic anhydride.

Particular preference is given to acrylic acid, methacrylic acid, acrylate esters with $C_1$- to $C_8$-alkyl, such as methyl acrylate, ethyl acrylate, n-butyl acrylate and 2-ethylhexyl acrylate, and methacrylic acid esters with $C_1$- to $C_8$-alkyl, such as methyl methacrylate.

Further suitable polymerizable compounds are dipropylene glycol diacrylate, tripropylene glycol diacrylate, polyethylene glycol diacrylate, glycerol triacrylate, ethoxylated glycerol triacrylate, trimethylolpropane triacrylate, ethoxylated trimethylolpropane triacrylate, butanediol monoacrylate, dicyclopentadienyl acrylate, 2-dimethylaminoethyl acrylate, 2-hydroxyethyl acrylate, 2-hydroxypropyl acrylate.

With acrylic acid as the polymerizable compound the total amount of the compounds of general formula (I) in the mixture is preferably from 0.0050% to 0.1000% by weight, preferably from 0.0100% to 0.0750% by weight, particularly preferably from 0.0120% to 0.0500% by weight, very particularly preferably from 0.0150% to 0.0250% by weight, in each case based on acrylic acid.

With methyl acrylate, methyl methacrylate, ethyl acrylate, n-butyl acrylate and/or 2-ethylhexyl acrylate as the polymerizable compound the total amount of the compounds of general formula (I) in the mixture is preferably from 0.0001% to 0.0100% by weight, preferably from 0.0002% to 0.0075% by weight, particularly preferably from 0.0005% to 0.0050% by weight, very particularly preferably from 0.0010% to 0.0020% by weight, in each case based on the total amount of methyl acrylate, methyl methacrylate, ethyl acrylate, n-butyl acrylate and/or 2-ethylhexyl acrylate.

The present invention further provides for the use of at least one compound of general formula (I) as defined hereinabove for polymerization inhibition of at least one polymerizable compound.

The present invention further provides a process for storage and/or transport of a mixture comprising at least one compound of general formula (I) as defined hereinabove and at least one polymerizable compound.

The mixture is normally stored and/or transported in an oxygen-containing atmosphere.

It is preferable when the mixture is stored in a vessel in an oxygen-containing atmosphere having an oxygen proportion of 5 to 10 vol % and the mixture is regularly recirculated in the vessel, for example by pumped recirculation of the entirety of the tank contents at least once per week. The relatively low oxygen proportion prevents formation of ignitable gas mixtures in the vessel. The recirculation replaces consumed dissolved oxygen in the liquid polymerizable compound.

EXAMPLES

The employed monomer was distilled twice to remove the polymerization inhibitor MEHQ. The obtained monomer was in each case admixed with the reported amount of the specified polymerization inhibitor.

0.5 ml of each mixture was transferred into a 1.8 ml ampoule and stored at the reported temperature in a recirculating air oven.

In each test series three ampoules of each mixture were filled and tested, wherein the average time for complete polymerization was determined by visual inspection.

Relative efficacy is calculated from the quotient of the time until polymerization of the sample with the polymerization inhibitor being tested and the time until polymerization of the sample with MEHQ. The efficacy of MEHQ itself is thus 100%.

The results are summarized in tables 1 to 6:

TABLE 1

Mixtures with acrylic acid

| Polymerization inhibitor | Amount | Temperature | Time until polymerization | Efficacy |
|---|---|---|---|---|
| MEHQ | 0.004% by wt. | 80° C. | 21.3 h | 100% |
| TMMP | 0.004% by wt. | 80° C. | 39.5 h | 185% |
| TMEP | 0.004% by wt. | 80° C. | 37.1 h | 172% |
| TMPP | 0.004% by wt. | 80° C. | 41.0 h | 190% |
| MEHQ | 0.004% by wt. | 90° C. | 6.1 h | 100% |
| TMMP | 0.004% by wt. | 90° C. | 10.3 h | 170% |
| MEHQ | 0.006% by wt. | 90° C. | 10.1 h | 100% |
| TMMP | 0.006% by wt. | 90° C. | 25.1 h | 250% |
| MEHQ | 0.006% by wt. | 80° C. | 27.4 h | 100% |
| DMMP | 0.006% by wt. | 80° C. | 40.1 h | 146% |

MEHQ: hydroquinone monomethyl ether
TMMP: 2,3,6-trimethyl-4-methoxyphenol
TMEP: 2,3,6-trimethyl-4-ethoxyphenol
TMPP: 2,3,6-trimethyl-4-propoxyphenol
DMMP: 2,6-dimethyl-4-methoxyphenol The polymerization inhibitors according to the invention exhibit improved efficacy compared to MEHQ. The polymerization inhibitors according to the invention simultaneously exhibit sufficient solubility in aqueous solutions, thus making acrylic acid stabilized with the polymerization inhibitors according to the invention suitable for producing aqueous polymer solutions. No cloudiness is observed.

TABLE 2

Mixtures with methacrylic acid

| Polymerization inhibitor | Amount | Temperature | Time until polymerization | Efficacy |
|---|---|---|---|---|
| MEHQ | 0.003% by wt. | 80° C. | 36.8 h | 100% |
| TMMP | 0.003% by wt. | 80° C. | 40.3 h | 110% |

TABLE 3

| Mixtures with methyl acrylate | | | | |
|---|---|---|---|---|
| Polymerization inhibitor | Amount | Temperature | Time until polymerization | Efficacy |
| MEHQ | 0.0005% by wt. | 80° C. | 18.9 h | 100% |
| TMMP | 0.0005% by wt. | 80° C. | >70 h | >370% |

TABLE 4

| Mixtures with ethyl acrylate | | | | |
|---|---|---|---|---|
| Polymerization inhibitor | Amount | Temperature | Time until polymerization | Efficacy |
| MEHQ | 0.0005% by wt. | 80° C. | 15.5 h | 100% |
| TMMP | 0.0005% by wt. | 80° C. | >70 h | >450% |

TABLE 5

| Mixtures with n-butyl acrylate | | | | |
|---|---|---|---|---|
| Polymerization inhibitor | Amount | Temperature | Time until polymerization | Efficacy |
| MEHQ | 0.0005% by wt. | 90° C. | 7.4 h | 100% |
| TMMP | 0.0005% by wt. | 90° C. | >70 h | >940% |

TABLE 6

| Mixtures with 2-ethylhexyl acrylate | | | | |
|---|---|---|---|---|
| Polymerization inhibitor | Amount | Temperature | Time until polymerization | Efficacy |
| MEHQ | 0.0005% by wt. | 90° C. | 6.0 h | 100% |
| TMMP | 0.0005% by wt. | 90° C. | 27.2 h | 460% |

The invention claimed is:

1. A mixture comprising at least one compound of formula (I), (I)

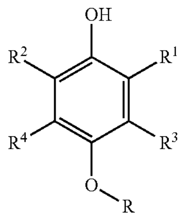

wherein

R is $C_1$- to $C_4$-alkyl $R^1$ is $C_1$- or $C_2$-alkyl and $R^2$ to $R^4$ are independently of one another H, $C_1$- or $C_2$-alkyl, and at least one polymerizable compound, wherein the at least one polymerizable compound is acrylic acid, methacrylic acid, methyl acrylate, ethyl acrylate, n-butyl acrylate, 2-ethylhexyl acrylate, methyl methacrylate, dipropylene glycol diacrylate, tripropylene glycol diacrylate, polyethylene glycol diacrylate, glycerol triacrylate, ethoxylated glycerol triacrylate, trimethylolpropane triacrylate, ethoxylated trimethylolpropane triacrylate, butanediol monoacrylate, dicyclopentadienyl acrylate, 2-dimethylaminoethyl acrylate, 2-hydroxyethyl acrylate, or 2-hydroxypropyl acrylate.

2. The mixture according to claim 1, wherein R and $R^1$ are independently of one another $C_1$- or $C_2$-alkyl and $R^2$ to $R^4$ are independently of one another H, $C_1$- or $C_2$-alkyl.

3. The mixture according to claim 1, wherein R is $C_1$- to $C_4$-alkyl, $R^1$ and $R^2$ are independently of one another $C_1$- or $C_2$-alkyl and $R^3$ and $R^4$ are independently of one another H, $C_1$- or $C_2$-alkyl.

4. The mixture according to claim 1, wherein R, $R^1$ and $R^2$ are independently of one another $C_1$- or $C_2$-alkyl and $R^3$ and $R^4$ are independently of one another H, $C_1$- or $C_2$-alkyl.

5. The mixture according to claim 1, wherein the compound of formula (I) is 2,3,6-trimethyl-4-methoxyphenol.

6. The mixture according to claim 1, wherein a total amount of the compounds of formula (I) in the mixture is from 0.0001% to 0.1000% by weight based on a total amount of polymerizable compounds.

7. The mixture according to claim 1, wherein a total amount of the polymerizable compounds is at least 5% by weight based on a total weight of the mixture.

8. The mixture according to claim 1, wherein the polymerizable compound is acrylic acid.

9. The mixture according to claim 8, wherein a total amount of the compounds of formula (I) in the mixture is from 0.0050% to 0.1000% by weight based on a total amount of acrylic acid.

10. The mixture according to claim 1, wherein the polymerizable compound is methyl acrylate, methyl methacrylate, ethyl acrylate, n-butyl acrylate and/or 2-ethylhexyl acrylate.

11. The mixture according to claim 10, wherein a total amount of the compounds of formula (I) in the mixture is from 0.0001% to 0.0100% by weight based on a total amount of methyl acrylate, methyl methacrylate, ethyl acrylate, n-butyl acrylate and/or 2-ethylhexyl acrylate.

12. A method comprising providing the at least one compound of formula (I) as defined in claim 1 and inhibiting polymerization of at least one polymerizable compound.

13. A process comprising storing and/or transporting the mixture according to claim 1.

14. The process according to claim 13, wherein the mixture is stored and/or transported in an oxygen-containing atmosphere.

15. The process according to claim 13, wherein the mixture is stored in a vessel in an oxygen-containing atmosphere having an oxygen proportion of 5 to 10 vol % and the mixture is regularly recirculated in the vessel.

16. The mixture according to claim 1, wherein R is $C_1$- to $C_4$-alkyl, $R^1$ and $R^2$ are each $C_1$-alkyl and $R^3$ and $R^4$ are independently of one another H, $C_1$- or $C_2$-alkyl.

* * * * *